United States Patent
Mayer et al.

(10) Patent No.: US 7,480,526 B2
(45) Date of Patent: Jan. 20, 2009

(54) METHOD FOR MAPPING AN EXAMINATION VOLUME IN AN MR SPECTROMETER

(75) Inventors: Klaus Mayer, Eckental (DE); Cecile Mohr, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 229 days.

(21) Appl. No.: 11/438,051

(22) Filed: May 19, 2006

(65) Prior Publication Data

US 2007/0016002 A1 Jan. 18, 2007

(30) Foreign Application Priority Data

May 19, 2005 (DE) .................. 10 2005 023 193

(51) Int. Cl.
*A61B 5/05* (2006.01)
(52) U.S. Cl. .................. 600/410; 600/413; 600/415; 324/309
(58) Field of Classification Search .............. 600/443, 600/413, 428, 409–411, 415; 324/309, 307; 424/306

See application file for complete search history.

(56) References Cited

U.S. PATENT DOCUMENTS

| 5,997,883 A * | 12/1999 | Epstein et al. ............ 324/306 |
| 6,292,684 B1 * | 9/2001 | Du et al. .................. 600/410 |
| 6,584,337 B2 * | 6/2003 | Dumoulin et al. .......... 600/410 |
| 6,897,655 B2 * | 5/2005 | Brittain et al. ............ 324/309 |
| 2002/0173715 A1 | 11/2002 | Kruger et al. |
| 2003/0036693 A1 * | 2/2003 | Avinash et al. ............ 600/413 |
| 2003/0178995 A1 * | 9/2003 | Peshkovsky et al. ........ 324/307 |

FOREIGN PATENT DOCUMENTS

WO WO 98/46132 10/1998

* cited by examiner

*Primary Examiner*—Eric F Winakur
*Assistant Examiner*—Lawrence N Laryea
(74) *Attorney, Agent, or Firm*—Schiff Hardin LLP

(57) ABSTRACT

In a method for mapping a large examination volume with an MR spectrometer, at least one examination segment in the examination volume is defined a positioning device is activated such that the examination segment is situated in an optimal measurement volume of the MR spectrometer. In order to improve the image quality, physiological events in the body of the patient are detected by a detection device, in which physiological events an acquisition state, in which an MR acquisition is possible, and a wait state in which no MR acquisition is possible, occur cyclically. In at least one wait state, the positioning device is moved such that the examination segment is situated in the optimal measurement volume of the MR spectrometer.

3 Claims, 4 Drawing Sheets

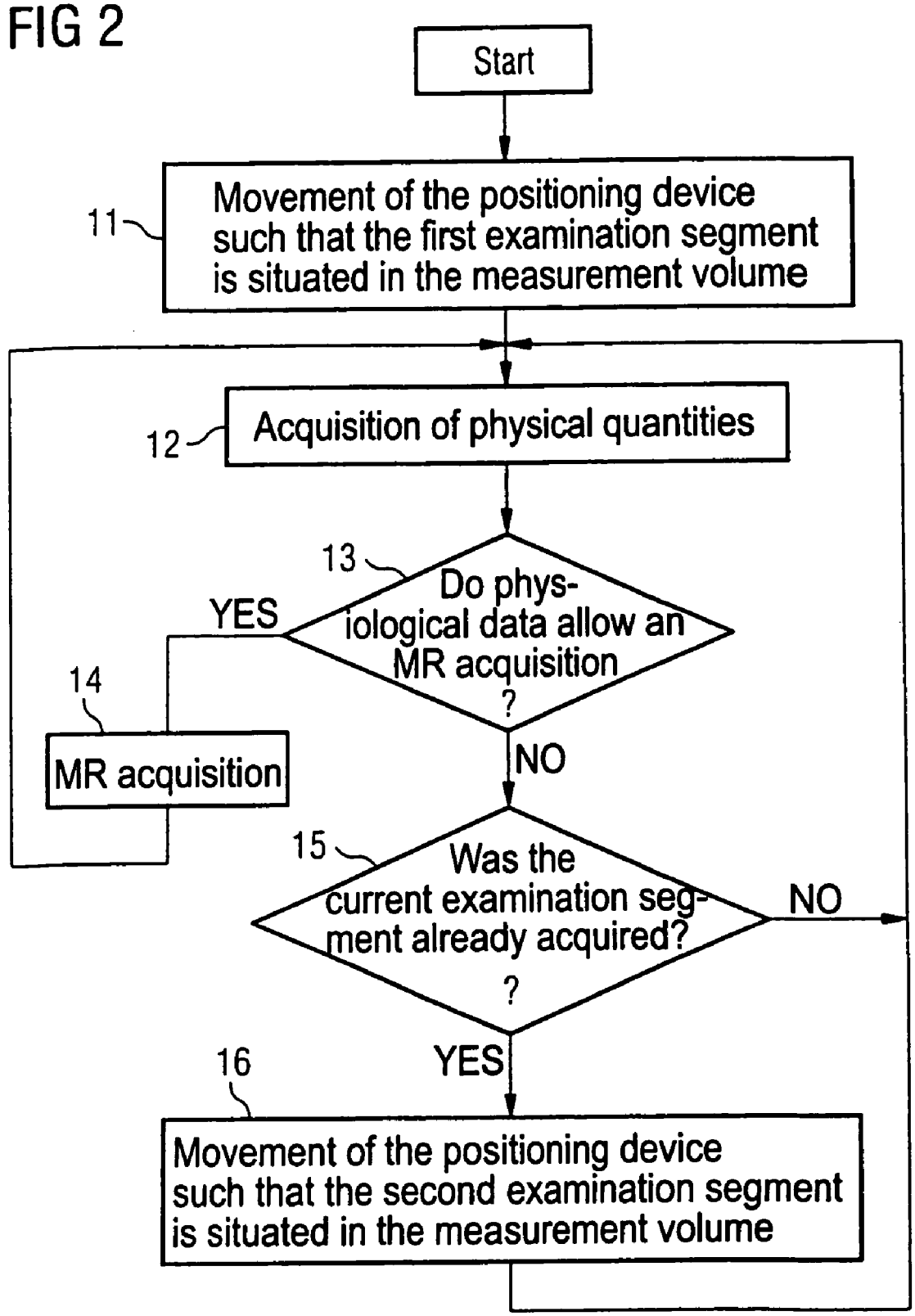

METHOD FOR MAPPING AN EXAMINATION VOLUME IN AN MR SPECTROMETER

BACKGROUND OF THE INVENTION

1. Field of the Invention

The present invention concerns a measurement in an MR spectrometer, and in particular a method for mapping an examination volume in an MR spectrometer.

2. Description of the Prior Art

Magnetic resonance (MR) measurements react sensitively to movements of the patient such as, for example, respiration movements of the abdomen and the thorax (ribcage). These movements lead to blurring and to degradations of the image quality.

An optimal image quality is achieved in MR measurements when the image of the measure is acquired in the isocenter of the basic field magnet, i.e. where the magnetic field is particularly homogeneous.

Modern MR systems are equipped with programmable positioning devices for the patient that allow movements over large anatomical regions in the measurement. These movements ensue step-by-step in discrete intervals or dynamically, meaning that the positioning device moves continuously through the magnet (Move During Scan, MDS). Moreover, measurements can also be implemented isocentrically, meaning that the positioning device automatically moves to the middle of the magnet.

Such MR measurement systems according to the prior art have the disadvantage that the image quality is subjected to physiological fluctuations.

SUMMARY OF THE INVENTION

An object of the present invention is to provide a method for mapping a large examination volume in an MR spectrometer, wherein the image quality is improved relative to the prior art.

This object is achieved in accordance with the invention by a method for controlling a positioning device so that physiological data of the patient are acquired in addition to the MR measurement. The existing physiological information is used in order to move the transport system such that an optimal image quality can be achieved. For this, the table movement with the stages "travel"/"stop"/"adjust speed" is synchronized with the respiratory cycle (inhale, exhale) or another physiological cycle (for example heart cycle, blood pressure, . . . ). The image quality can be very efficiently improved.

The inventive method for mapping a large examination volume with an MR spectrometer includes the steps of defining at least one examination segment in the examination volume and activation of a positioning device such that the examination segment is situated in an optimal measurement volume of the MR spectrometer; the measurement volume being defined detection of physiological events in the body of the patient by a detection device. The measurement volume may be in an acquisition state for which an MR acquisition is possible or a wait state in which no MR acquisition is possible, these states occurring cyclically. In the at least one wait state, the positioning device is moved such that the examination segment is situated in the optimal measurement volume of the MR spectrometer, for subsequent data acquisition.

The physiological event is in particular the respiration and the detection device is in particular a respiration frequency detection device. The acquisition state corresponds to the exhalation and the wait state corresponds to the inhalation. This allows an MDS (move during scan) data acquisition.

Alternatively, cardiac activity can be used as the physiological event and a heart frequency detection device can used as the detection device, and the acquisition state corresponds to the diastolic phase of the blood pressure (cardiac cycle) and the wait state corresponds to the systolic phase of the blood pressure.

Among other things, the inventive method has the advantage that the measurement time can be shortened since the "dead time" between the individual measurement steps is used in order to bring the patient into a new measurement position, such that the total measurement time is used more effectively.

DESCRIPTION OF THE DRAWINGS

FIG. 2 shows an exemplary embodiment of the inventive method for positioning of a patient in an MR spectrometer.

The representation in the figures is not to scale.

DESCRIPTION OF THE PREFERRED EMBODIMENTS

As an example, the invention is described in the following using a respiration cycle.

Figure 1A:
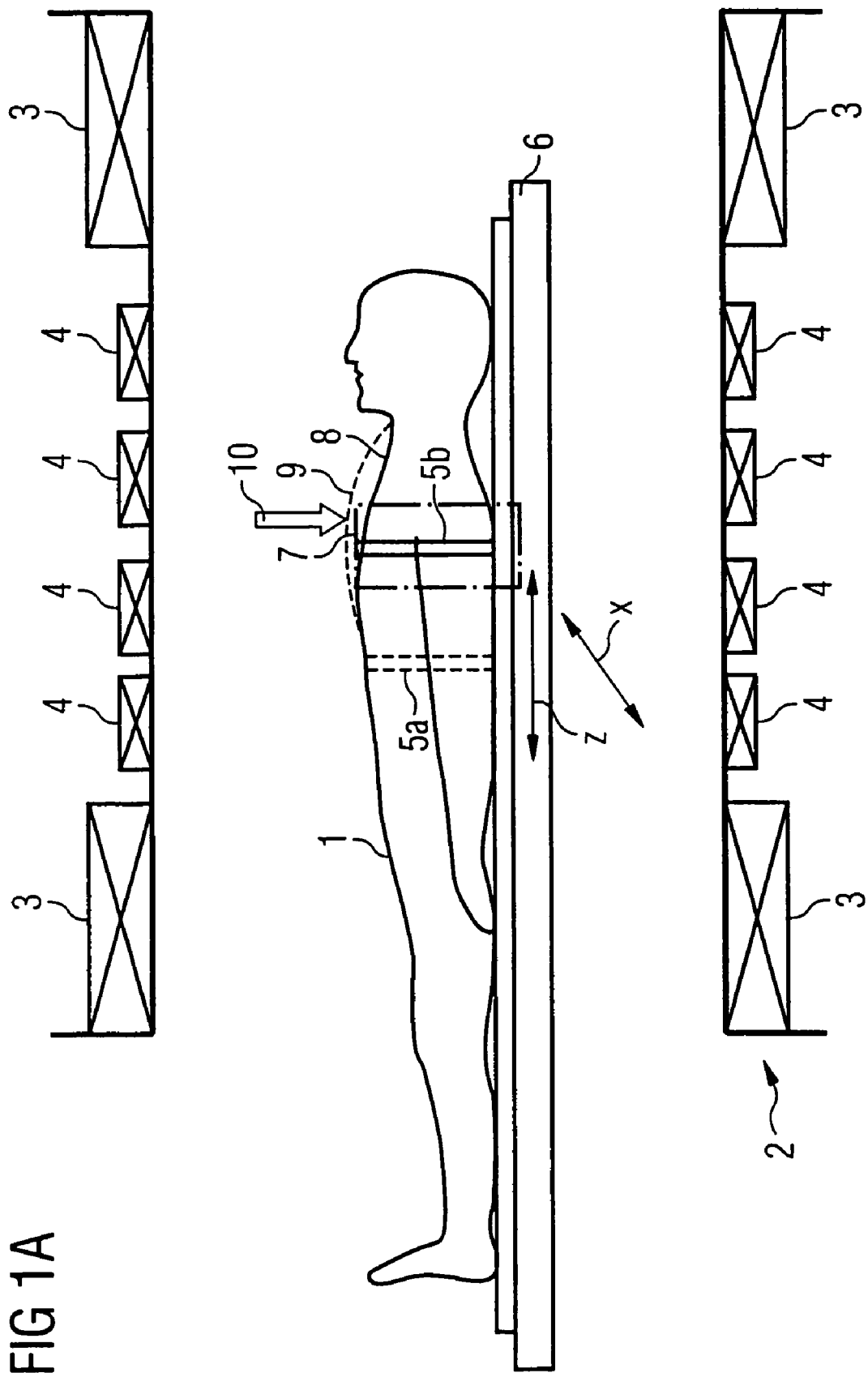
FIGS. 1A and 1B respectively, schematically show the inventive positioning of a patient in an MR spectrometer in a first position and in a second position.

In FIG. 1A, a patient is shown as a large examination volume 1 of which exposures are to be made with an MR spectrometer 2.

The MR spectrometer 2 has a superconducting shielding coil 3 at the entrance and at the exit. A number of superconducting field coils 4 are located between the two shielding coils 3. A magnetic field that enables the MR measurement (data acquisition) is generated by these coils 3 and 4. An optimally homogeneous magnetic field is necessary for a good image quality. The magnetic field generated in the MR spectrometer by the coils 3 and 4 is particularly homogeneous in a measurement volume 7. This measurement volume 7 is shown in FIG. 1A as a box with a dashed outline.

In order to be able to make an exposure of a large region of the examination volume 1 (i.e. here the patient), a number of examination segments (of which both segments 5a and 5b are schematically shown in FIG. 1A) are defined in this examination volume 1. These examination segments 5a and 5b are successively brought into congruence with the measurement volume 7 in which the optimal conditions exist for ad MR acquisition.

For this, the patient is placed on a positioning device or a table 6 and the positioning device 6 is displaced such that, for example, the examination segment 5a arrives in congruence with the measurement volume 7 of the MR spectrometer 2.

An optimal image quality is therewith ensured.

Figure 1B:
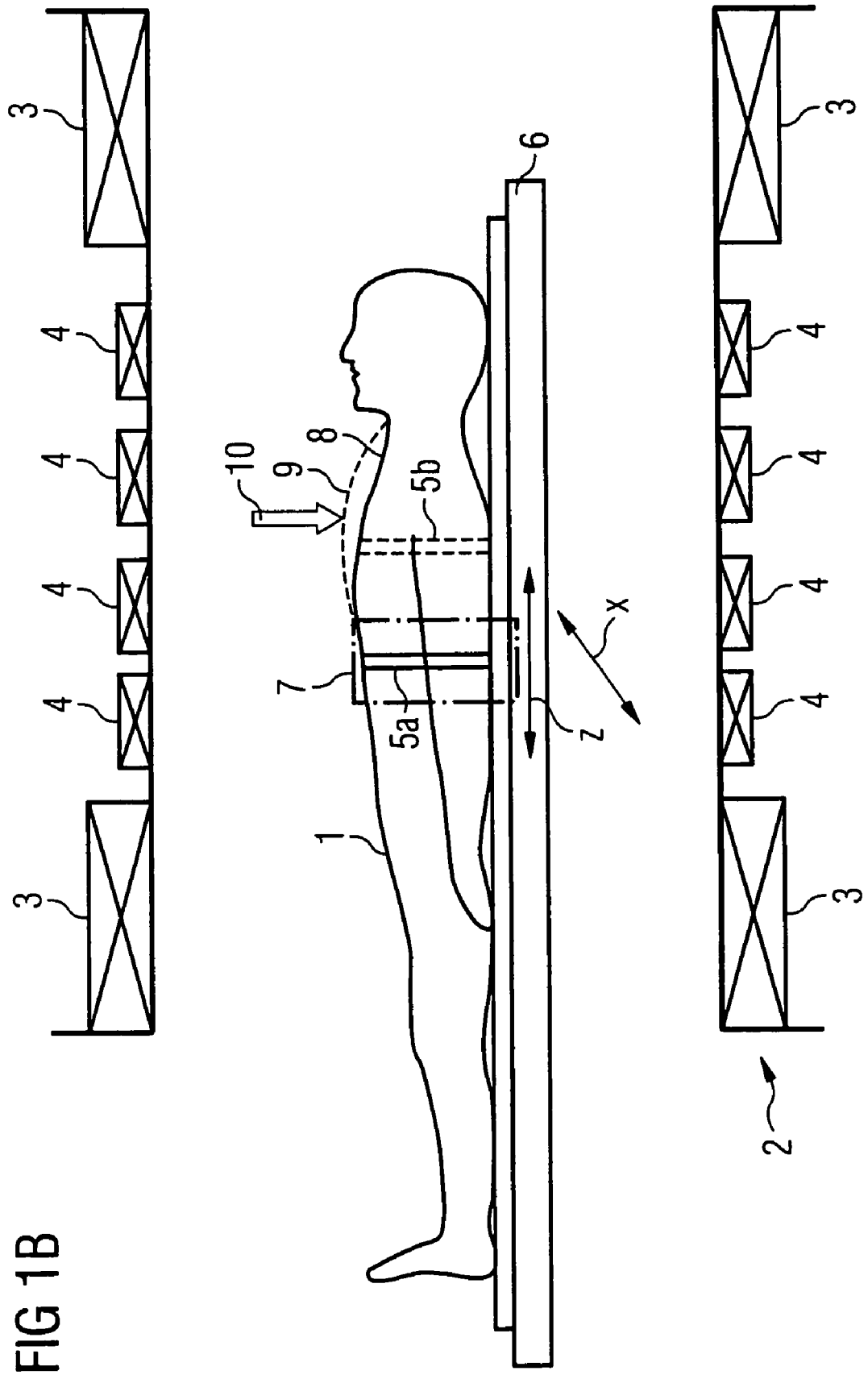

When the examination segment 5b should is to be subsequently acquired, the positioning device 6 is displaced such that now the examination segment 5b arrives in congruence with the measurement volume 7. This is schematically shown in FIG. 1B. The movement can proceed parallel to the main axis of the magnetic field (i.e. in the z-direction) or it can proceed transversely to this direction (for example in the x-direction). If applicable, the positioning device 6 can be displaced in terms of height (not shown).

The displacement of the positioning device 6 is inventively synchronized with physiological events in the body of the patient in a cycle in which an acquisition state occurs, in which an MR acquisition is possible, and in which a wait state occurs, in which no MR acquisition is possible.

For this purpose, the aforementioned physiological events are detected by a detection device 10. When it is detected in the detection that the current physiological state allows a MR exposure, MR data are acquired (acquisition state). By contrast, if it is established by the detection that the current physiological state of the patient does not allow such an exposure, according to the invention this detection is utilized in order to trigger displacement of the patient in this rest phase such that the next examination segment 5b is located in the "focus" of the MR spectrometer. This means that the positioning device 6 is moved in the wait state such that, after the movement, the next examination segment 5b is situated in the measurement volume 7 of the MR spectrometer 2 for an acquisition with optimal image quality.

In FIGS. 1A and 1B, the invention is illustrated with respiration being used as the physiological event and a respiration frequency detection device is used as the detection device 10. This is indicated in FIG. 1A and FIG. 1B by a block arrow directed toward the thorax of the patient. In this embodiment, the positioning device 6 is stopped upon exhalation. The movement of the positioning device 6 is continued when the respiration cycle of the patient is essentially again in the same phase in which a preceding exposure was acquired (MDS measurement). In other words, the acquisition state corresponds to the exhalation and the wait state corresponds to the inhalation.

Other physiological events can also be used as a "trigger". Cardiac activity can also be used, and a heart frequency detection device, a pulse frequency detection device or a blood pressure detection device or the like can be used as a detection device 10. In a further preferred embodiment of the invention, the heart activity is detected by a heart frequency detection device (not shown), and the acquisition state corresponds to the diastolic phase of the blood pressure and the wait state corresponds to the systolic phase of the blood pressure.

The workflow of an embodiment of the inventive method for acquisition of an MR spectrum is shown in FIG. 2.

In a step 11, the positioning device 6 is moved such that a first examination segment (for example 5a) is situated in the measurement volume 7 of the MR spectrometer. In a step 12, physiological data are subsequently acquired in the MR measurement, and the image quality of the measurement result could be impaired. The differentiation into states that are advantageous and less advantageous for the MR measurement follows in the step 13, in which it is queried whether an MR measurement is possible. In the event that this is the case, the method jumps to the step 14 in which the actual measurement is implemented. A jump back to the acquisition of physiological data in step 12 subsequently ensues.

If it is established in step 13 that the acquired physiological data allow no MR acquisition, in a further step 15 it is checked whether the current examination segment (meaning that which is immediately located in the measurement volume 7) has already been acquired. If this is not the case, the system must wait for a more advantageous point in time for a measurement, and a jump back to the acquisition of physiological data in step 12 therefore follows. In step 13 it is checked whether an MR acquisition is possible.

By contrast, if it is established in step 15 that the examination segment that is immediately located in the measurement volume 7 has already been acquired, the "dead time" in which no MR measurement is possible is used in a step 16 in order to move the positioning device 6 such that the next examination segment 5b is moved into the measurement volume 7. A jump back to the acquisition of physiological data in step 12 follows again.

The table movement and, for example, the respiration phases are thus inventively synchronized. This synchronization can be implemented in conventional ("static") measurements and also in MDS acquisitions.

Conventional ("static") measurements mean that the positioning device is moved such that the examination segment 5a or 5b is always located in the isocenter of the magnet. This is particularly of importance for axial examinations of the abdomen. There is no longer a time loss since the table movement is effected in the times that are otherwise physiological "dead times" (for example exhalation). The possibility exists to implement studies with a number of breath-hold phases in a simple manner where the system uses the "dead times" to move into the isocenter. The image quality can be clearly improved in this manner.

In MDS measurements, the system automatically synchronizes with the respiration or with other physiological events that otherwise contribute to a degradation of the image. Extraordinarily good image qualities are thus also achieved given this measurement method.

In detail, this means that a program uses the respiration information from the detection device 10 in conventional ("static") measurements. When an exhalation event is detected by the detection device 10, a command is output to the positioning device 6 so that the table is moved in the "isocenter" function such that the acquisition of the next section 5b in the measurement volume 7 can ensue. For example, this can always occur when the patient holds his or her breath. The system detects that the patient is holding his or her breath, and an automatic movement to the middle of the next section for the next acquisition is implemented.

This is particularly advantageous when axial exposures of the abdomen are to be made and the positioning device 6 is displaced in the z-direction (direction of the magnetic field), such that the slice planes are respectively repositioned at the optimal position in the magnet (i.e. in the measurement volume or the isocenter 7) in order to improve the image quality.

In MDS measurements, the table is moved continuously. The patient holds his breath in phases. In the systems according to the prior art, in the MR measurement the respiration is additionally monitored with a "navigator" signal or a respiration girdle. In both cases, it is detected in this manner wither the patient inhales or exhales. The data acquisition is typically interrupted during the exhalation phase and resumed during the inhalation phase. The positioning device 6 moves during the inhalation or breath-hold phases and data are acquired. In order to interrupt the measurement (and therewith the movement of the positioning device 6) at the correct time, when the patient is holding his or her breath, in the prior art the operating personnel of the MR spectrometer must ask the patient to exhale. The movement of the positioning device 6 is then stopped, and the movement is only resumed when the respiration cycle of the patient is in a phase similar to that in which the prior data was acquired. It is thereby ensured that all data are acquired in a comparable physiological state and thus that the image quality is optimal.

In the inventive method, the system automatically detects when the patient exhales and the movement is interrupted. As soon as the patient holds his breath again, the acquisition begins again. An intervention of the operating personnel for the MR spectrometer is no longer necessary.

With this, 1) the "dead time" during the respiration-synchronized acquisitions is used in order to move the table into the isocenter of the magnet where the homogeneity of the magnetic field (and therewith the image quality) are best, and 2) the respiration information is used in order to intelligently control the table movement in MDS acquisitions such that the image quality is maximized.

By contrast, in conventional measurements the "dead time" that is present during the exhalation phase is not used by the MR system. In acquisitions in MDS operation (which was previously still in the development phase) in the prior art, the information about the respiration is thus not used in order to position the table and ultimately to stop it in order to improve the image quality.

Figure 3A:
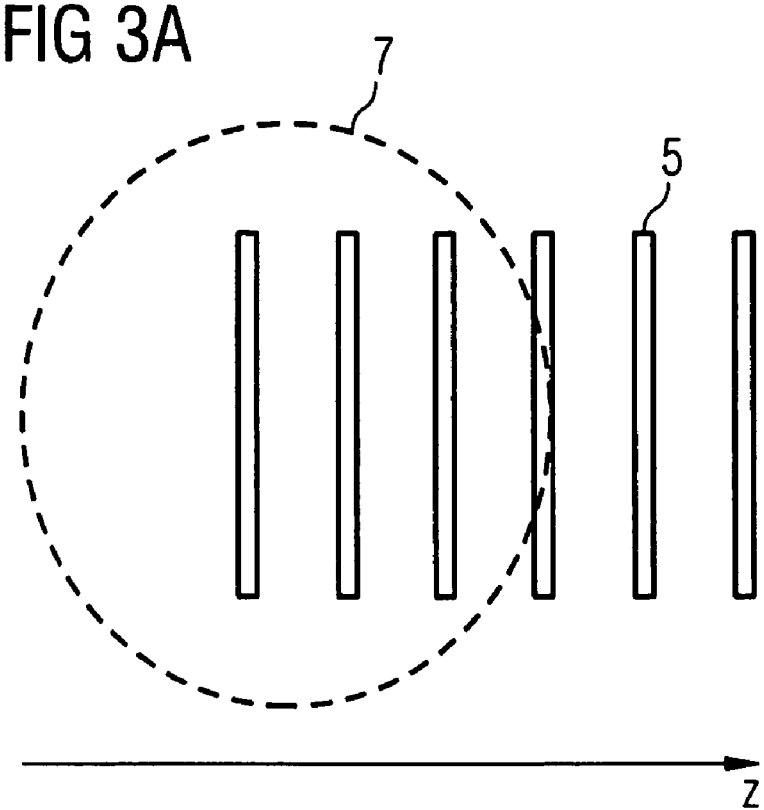
FIG. 3A and FIG. 3B show a practical example for an MR acquisition in a spectrometer for explanation of an embodiment of the inventive method.
Figure 3B:
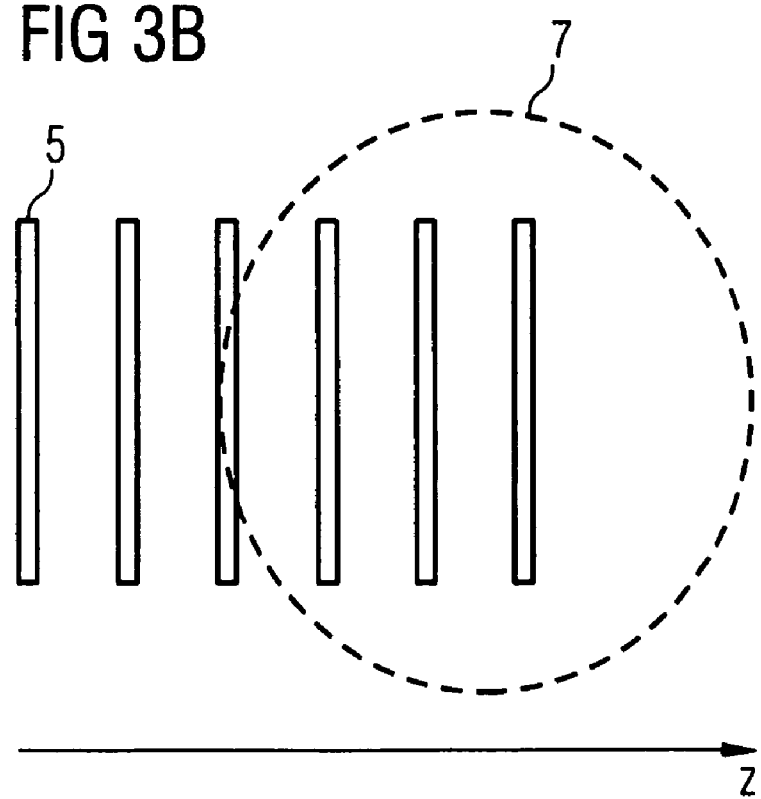

For further explanation, a practical example for an MR acquisition in a spectrometer is shown in FIG. 3A and FIG. 3B. A first situation is shown in FIG. 3A. Three examination segments 5 are located in the measurement volume 7 (shown here as oval and not as rectangular). Three further examination segments 5 are located at least partially outside of the measurement volume 7. Of course, the outline of the measurement volume 7 is meant only symbolically and does not represent a precise physical limit. After the three examination segments 5 have been acquired in the measurement volume 7, the positioning device 6 moves in the negative z-direction. Its end position is shown in FIG. 3B. As soon as the exhalation is ended and the patient begins with the inhalation, the three next examination segments 5 that are now located in the measurement volume 7 are acquired. An optimal image quality is thereby obtained in the acquisition of large examination volumes that are to be acquired in segments. In reverse, for example, the patient is moved in the positive z-direction with the positioning device after the exhalation in FIG. 3B. The end position can now correspond to the representation in FIG. 3A, and after the exhalation those examination segments 5 that are located in the measurement volume 7 in the position of the positioning device 6 shown in FIG. 3A are acquired upon inhalation.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for obtaining magnetic resonance data from a large examination volume, comprising the steps of:
    defining a plurality of examination segments of a patient, from which MR spectroscopic data are to be acquired with respect to an examination volume of an MR data acquisition unit;
    using a positioning device on which the patient is disposed, positioning the patient relative to said measurement volume of said MR data acquisition unit so that a first of said examination segments is situated in said measurement volume;
    with a detection device, detecting a signal representing a cyclical physiological event in said patient, said cyclical physiological event comprising cyclically occurring acquisition states, in which an acquisition of said MR data is possible, and wait states, in which an acquisition of said MR data is not possible; and
    controlling said positioning device using said signal so that after said MR data are acquired from a first of said plurality of examination segments, said positioning device with the patient thereon is moved, during one of said wait states, to situate a next examination segment in said plurality of examination segments in said measurement volume of said MR data acquisition unit.

2. A method as claimed in claim 1 wherein said physiological event is respiration, and comprising detecting a respiration frequency signal as said signal, and wherein said acquisition states represent exhalation and said wait states represent inhalation by the patient.

3. A method as claimed in claim 1 wherein said physiological event is cardiac activity, and comprising detecting cardiac frequency as said signal, with said acquisition states corresponding to the diastolic phase and the wait states corresponding to the systolic phase of said cardiac cycle.

* * * * *